(12) United States Patent
Sano et al.

(10) Patent No.: US 6,818,756 B2
(45) Date of Patent: Nov. 16, 2004

(54) GENE WHICH EXHIBITS INDUCED EXPRESSION BY STRESS

(75) Inventors: Hiroshi Sano, Ikoma (JP); Tomonobu Kusano, Nara (JP)

(73) Assignee: Nara Institute of Science and Technology, Nara (JP)

( * ) Notice: Subject to any disclaimer, the term of this patent is extended or adjusted under 35 U.S.C. 154(b) by 0 days.

(21) Appl. No.: 09/805,919

(22) Filed: Mar. 15, 2001

(65) Prior Publication Data

US 2003/0096416 A1 May 22, 2003

(30) Foreign Application Priority Data

Mar. 15, 2000 (JP) ........................................ 2000-071655

(51) Int. Cl.[7] .......................... C12N 15/29; C12N 15/82
(52) U.S. Cl. ...................................... 536/23.6; 800/289
(58) Field of Search ......................... 536/23.6; 800/289, 800/278

(56) References Cited

PUBLICATIONS

Lee et al. A highly conserved kinase is an essential component for stress tolerance in yeats and plant cells. May 1999, Proc. Natl. Acad. Sci. USA, vol. 96, pp. 5873–5877.*

* cited by examiner

*Primary Examiner*—Phuong T. Bui
*Assistant Examiner*—Cynthia Collins
(74) *Attorney, Agent, or Firm*—Burns, Doane, Swecker & Mathis, L.L.P.

(57) ABSTRACT

A novel gene useful for production of a plant exhibiting resistance to environmental stress is provided. According to this invention, C7 gene, a novel gene encoding a receptor-like protein which is induced in response to injury stress, osmotic pressure stress, salt stress or low-temperature stress, is provided. Moreover, a polypeptide encoded by this gene is provided. A plant exhibiting resistance to environmental stress can be produced by incorporation of this novel gene into the plant.

2 Claims, 5 Drawing Sheets

```
C7              SKAQDISQG VPSSC--GDI  QIKFPFRT DPEHCGRRGY  HLDEQNNQIL
LRK10 homolog 1 SDEADFFRNC FPSRGSSDGP  LIKFPFRTES SSSSCHAPCM  CHSCSGQHIL
LRK10 homolog 2 SDEADFFRNC FPSRGSSDGP  DIKFPFRIES SSSSCHAPCM  CHSCSGQHIL C7              VFNYKSRIFD VPEINY---R  SYSIRLLDP- ---D        QRENCIVFPN
LRK10 homolog 1 LLHHVLGLSK VTGLIYYIYGV INIMFLAESW SQCALQKIIS  ANYSTSVYKQ
LRK10 homolog 2 LLHHVLGLSK VTGLIYIYGV  INIMFLAESW SQCALQKIIS  ANYSTSVYKQ C7              HRASIDAMT- SQIHEWVRV  NNDINYVNCI APINSQMI-   FLSEQS
LRK10 homolog 1 YGFQVASHVS QSHEHMDST  DSIFGPTSCI SNASQSIYLV  ADYAHMS
LRK10 homolog 2 YGFQVASHVS QSHEHMDST  DSIFGPTSCI SNASQSIYLV  ADYAHMS
```

FIG. 4
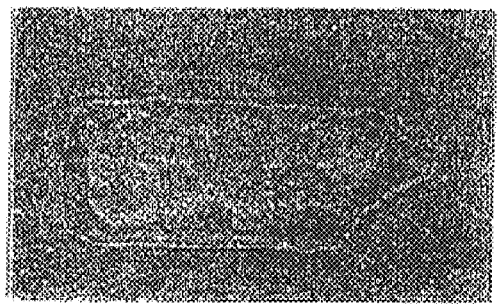 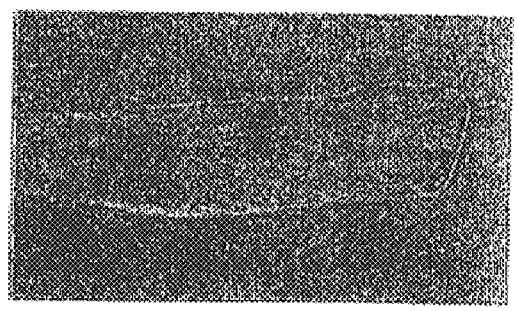
GFP C7-GFP

GENE WHICH EXHIBITS INDUCED EXPRESSION BY STRESS

BACKGROUND OF THE INVENTION

1. Field of the Invention

This invention relates to C7 gene, a novel gene induced in response to injury stress, osmotic-pressure stress, salt stress or low-temperature stress, which encodes a receptor-like protein.

2. Description of the Art

In the future, technical development for efficient production of crops in agriculture will be required, because food crisis is expected to occur. Since loss of food production caused by various environmental stresses is a serious problem in the field of agriculture, there is great demand on production of a plant exhibiting tolerance to various environmental stresses.

To attain such a purpose, it is indispensable to investigate on self-defense system against stresses in a plant. The self-defense system can be roughly classified to the following three stages: (1) recognition of stress; (2) transduction of stress signal; and (3) response to stress. The investigation on the second process of signal transduction and third process response have achieved some progression and factors involved in the processes were identified. However, the knowledge on the first recognition process and the relation of the process with the signal transduction process remains to be insufficient. In general, it is known that an upstream factor operates to control plural downstream factors in the signal transduction pathway. Therefore, it is considered that the analysis on the recognition process, which exists in the upstream of the pathway, might give a method for efficient and concurrent control of plural factors, at the transduction pathway or the recognition pathway locating downstream of the stress defense mechanism.

SUMMARY OF THE INVENTION

Therefore, the inventors investigated on a method to render stress resistance to a plant, using factors operating in the process of stress recognition in a plant. That is, the object of this invention is isolation of a gene involved in early stage of stress response and analysis of the mechanism of the function of the gene.

The inventors searched for a gene induced by exposure to stresses, those are injury stress, osmotic-pressure stress, salt stress and low-temperature stress (4° C.), using tobacco (Nicotiana tabacum cv Xanthi nc). As the result, the inventors obtained C7 gene temporarily induced by those stresses in its early stage. That is, C7 gene of this invention was initially identified by FDD method as a rapidly and transiently induced clone upon wounding. Using this FDD fragment, the full-length cDNA clone was isolated from a cDNA phage library prepared from wounded tobacco plants. From the viewpoint of the expressive response of C7 gene, it is assumed that the product of said gene may be a sensor which recognizes external stress and involved in expression control of stress responsive gene existing its downstream. Therefore, it is expected that, a plant exhibiting resistance to injury stress, osmotic-pressure stress, salt stress or low-temperature stress might be produced by incorporating said gene into a plant.

BRIEF EXPLANATION OF THE DRAWINGS

FIG. 1 a figure showing the total base sequence and the deduced amino acid sequence of C7 gene.

FIG. 3 is a figure showing amino acid alignment of the region exhibiting homology to LRK10, a receptor-like protein.

FIG. 4 is a photograph showing expression of C7-GFP fusion protein on cell surface.

DETAILED DESCRIPTION OF THE PREFERRED EMBODIMENTS

Figure 2:
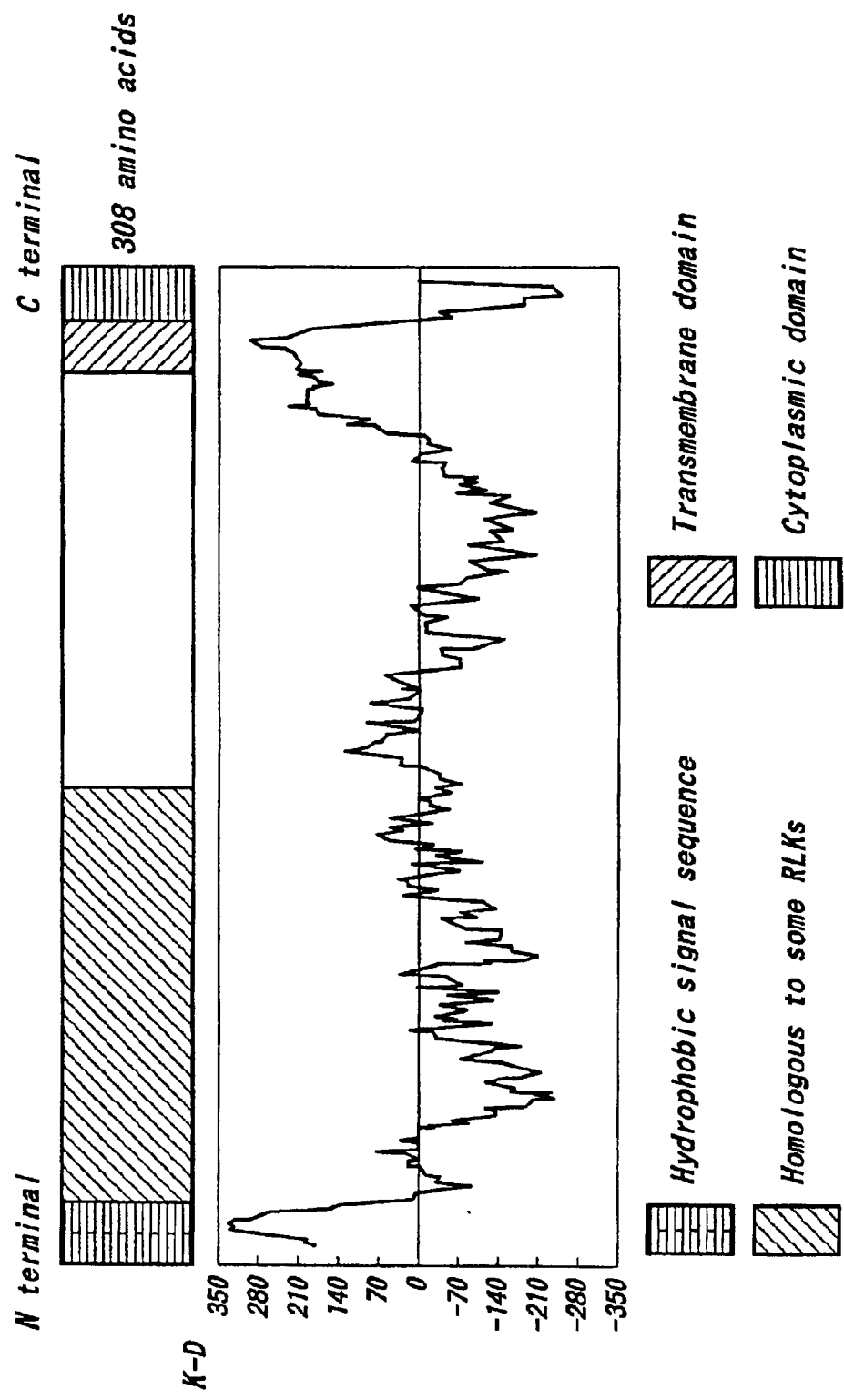
FIG. 2 is a figure showing predicted functional region and hydrophobic profile of C7 gene product.

This invention relates to C7 gene originated from tobacco, consisting of a base sequence consists of bases numbered by Nos. 1–1210 shown in SEQ ID NO: 3 in a sequence list thereof. The C7 gene has the characteristic that its expression is induced by injury stress, osmotic-pressure stress, salt stress or low-temperature stress. In the C7 gene, the base sequence corresponding to open reading frame portion, the portion encoding the protein, is shown in SEQ ID NO: 2 in a sequence list thereof. The gene consisting of the base sequence shown in SEQ ID NO: 2 in a sequence list thereof is also within the range of this invention.

According to technique of gene recombination, artificial modification can be achieved at a specific site of basic DNA, without alteration or with improvement of basic characteristic of said DNA. Concerning a gene having native sequence provided according to this invention or modified sequence different from said native sequence, it is also possible to perform artificial modification such as insertion, deletion or substitution to obtain gene of equivalent or improved characteristic compared with said native gene. Moreover, a gene with such mutation is also included in the range of this invention. That is, the gene, consisting of a base sequence hybridizes with said base sequence shown in SEQ ID NO: 3 in a sequence list thereof under stringent condition, means a gene in which 20 or less, preferably ten or less, and more preferably five or less bases of the sequence is deleted, substituted or added to the base sequence shown in SEQ ID NO: 3 in a sequence list thereof. Moreover, such gene exhibits homology 60% or more, preferably 70% or more and still preferably 80% or more with the base sequence shown in SEQ ID NO: 3 in a sequence list thereof. In addition, such gene hybridizes with the base sequence shown in the SEQ ID NO: 3 in a sequence list thereof under stringent condition. Such gene is also within the range of this invention so far as it exhibits the characteristic of C7 gene, being induced by stresses described above.

Furthermore, this invention relates to C7 polypeptide originated from tobacco, consisting of an amino acid sequence consists of amino acids numbered by NOS. 1–308 shown in SEQ ID NO: 1 in a sequence list thereof. The polypeptide is encoded by the open reading frame portion of the base sequence indicated by SEQ ID NO: 2 in a sequence list thereof. The poly-peptide consisting of an amino acid sequence in which a part of said poly-peptide consists of amino acid sequence shown in SEQ ID NO: 1 is deleted, substituted or added with one or more amino acids means a polypeptide in which 20 or less, preferably ten or less, and more preferably five or less amino acids of the sequence is deleted, substituted or added to the amino acid sequence shown in SEQ ID NO: 1 in a sequence list thereof. Moreover, such polypeptide exhibits homology 60% or more, preferably 70% or more and still preferably 80% or more with the amino acid sequence shown in SEQ ID NO: 1 in a sequence list thereof. Such polypeptide is also within the range of this invention so far as it exhibits characteristic as C7 polypeptide, being induced by injury stress, osmotic-pressure stress, salt stress or low-temperature stress.

A method to transform a plant by incorporating C7 gene into a plant, and a transgenic plant produced by incorporation of said C7 gene are also within the range of this invention. The C7 gene of this invention is a gene induced by injury stress, osmotic-pressure stress, salt stress or low-temperature stress and it is involved in self defense mechanism of a plant. Therefore, resistance to salt stress can be rendered to a plant by incorporating said gene into a plant. The example of plants, preferred as a target plant, to which said gene induced by salt stress of this invention is incorporated, may include monocotyledonous plants, such as a lily, rice, maize, asparagus and wheat, as well as dicotyledonous plants, such as *Arabidopsis thaliana*, tobacco, carrot, soybean, tomato and potato.

A conventional method known in this art, as a method to produce a transformant, can be utilized. A vector available in this invention may include a plasmid vector, such as pBI121 and pBI221, but not limited to them. Such vector can be incorporated into an Agrobacterium strain, then a callus or a plantlet can be transfected by the Agrobacterium strain to produce a transgenic plant. Furthermore, a seed from such transgenic plant can be obtained. The method to incorporate said plant gene of this invention is not limited to Agrobacterium method and other methods, such as particle gun method and electroporation method, can be also utilized for incorporation of the gene.

EXAMPLES (Isolation of C7 gene fragment)

The gene involved in initial response of injury stress was isolated using the fluorescence differential displaying (FDD) method. Using the FDD method, the C7 gene fragment, temporarily induced in early stage of injury, was obtained. The C7 gene fragment was recovered from the gel, reamplified by PCR using the same pair of primers. The amplified fragment was cloned into pGEM-T easy vector (Promega), resulting in the clone C7-1. Southern hybridization on a blot of the original FDD-band pattern and northern hybridization reveals that the clone C7-1 contains a correct fragment. The sequence of the fragment, consisting of 338 bp, was determined by DNA sequencing.

(Southern Hybridization)

Southern hybridization analysis was performed, using the clone (C7-1) obtained by the method mentioned above, as a probe. The DNA fragmen amplified by PCR method, was applied to gel electrophoresis using 1% agarose/0.5×TBE. The gel was stained by ethidium bromide solution and the reaction product was confirmed on trans-illuminator. DNA fragments were recovered according to the protocol of Prep-A-Gene-DNA refining kit (BioRad). The DNA probe was radio-labeled using BcaBEST labeling kit (TAKARA) and radio-labeled DNA probe was prepared. Membrane was placed in a vessel and hybridization solution was added into the vessel and pre-hybridization was performed at 65° C. for more than 1 hour. Then hybridization was performed at 65° C. for more than 16 hours using the radio-labeled DNA probe prepared in the vessel. After washing the membrane, analysis using bio-image analyzer was performed.

(Northern Hybridization)

Membrane was placed in a vessel and hybridization solution was added into the vessel and pre-hybridization was performed at 42° C. for more than 1 hour. Hybridization was performed at 42° C. for more than 16 hours using the radio-labeled DNA probe prepared in the vessel. After washing the membrane, analysis using bio-image analyzer was performed.

(Preparation of cDNA Library)

(RNA Extraction)

RNA was extracted from tobacco leaf 45 minutes after exposure to injury stress, using acid guanidium thiocyanate/phenol/chloroform method (AGPC method). Intact tobacco leaves were cut into 5 $cm^2$ of pieces by scissors and they were allowed to float on distilled water. The leaf pieces were collected after 45 minutes and they were frozen in liquid nitrogen. Tobacco leaves, equivalent to fresh weight 1 g, was put into a triturator and it was fractured enough to be powder form in the triturator, allowing it to freeze with liquid nitrogen. The powder was put into a tube containing denaturing buffer and 2-mercaptoethanol, then the mixture was homogenized by POLYRON. One ml of 2M NaOAc (pH 4.0) was added to it and then stirred, and subsequently 10 ml of acid phenol was added and stirred. Then, 2 ml of chloroform/isoamyl alcohol (IAA) (49:1) was added to it and stirred, and it was left on ice for 15 minutes. After centrifugation, the aqueous layer was removed, 10 ml of isopropanol was added and the resulting solution was left in the room temperature for 10 minutes. After centrifugation, the pellet was dissolved in 600 $\mu$l of diethylpyrocarbonate (DEPC) treated water and the solution was transferred to centrifugal tube. Six hundred $\mu$l of phenol/chloroform/IAA (25:24:1) was added to it and centrifuged, then the aqueous layer was harvested. This operation was repeated twice. Two hundred $\mu$l of 8M LiCl was added to it and the mixture was left at 4° C. for 4 hours. After centrifugation, the supernatant was removed. One ml of 70% ethanol was added to the precipitation. After centrifugation, the supernatant was removed, then, it was allowed to dry in speed-back concentrator. The precipitation was dissolved in 50 $\mu$l of DEPC treated water to obtain total RNA extract.

(Purification of mRNA)

Purification was performed according to the protocol of mRNA purification kit (Pharmacia). The total RNA extract was re-dissolved in 1 ml of elution buffer. The column was re-suspended, then a falcon tube was stood vertically and 1 ml of high salt buffer was allowed to elute with gravity. This operation was repeated twice. The total RNA sample was denatured by heat treatment at 65° C. for 5 minutes, immediately it was cooled on ice. Then 0.2 ml of sample buffer was applied to the column, the buffer was allowed to elute with gravity, then centrifuged. Two-hundred and fifty $\mu$l of high salt concentration buffer of was applied, then centrifuged. This operation was repeated 3 times. Two-hundred and fifty $\mu$l of low salt concentration buffer was applied, then centrifuged. This operation was repeated 3 times. The column was taken out from the falcon tube and the elute was removed. Again the column was stood vertically, 250 $\mu$l of elution buffer incubated at 65° C., was applied and mRNA fractions were recovered by centrifugation. This operation was repeated 4 times. Operation of the above-mentioned spun column chromatography was repeated twice. Hundred $\mu$l of sample buffer, 10 $\mu$l of glycogen solution and 2.5 ml of ice-cooled 100% ethanol were added to the recovered RNA fraction and it was stand at −20° C. for more than 2 hours.

The supernatant was removed by centrifugation and the precipitate was dissolved in 1 ml of elution buffer to obtain purified mRNA sample.

(Synthesis of First Strand)

The purified mRNA sample, corresponding to 5 μg, was dissolved in 11 μl of DEPC treated water and 2 μl of linker primer was added to it. After incubation at 70° C. for 5 minutes, it was cooled on ice immediately. Ten μl of 5× first strand buffer, 3 μl of first strand methyl nucleotide mixture, 5 μl of 0.1M DTT, 1 μl of RNase block ribonucleotide inhibitor, and 12 μl of DEPC treated water were added to it in the order. Then it was mixed and incubated at 37° C. for 2 minutes. SUPERSCRIPT II reverse transcriptase was added to it and mixed. After 1 hour of reaction, it was cooled on ice.

(Synthesis of Second Strand)

The synthesis was performed according to the protocol of ZAP-cDNA synthesis kit (Stratagene). Twenty μl of 10× second strand buffer, 6 μl of second strand nucleotide mixture, 111 μl of distilled water, 2 μl of RNaseH and 12 μl of DNA-polymerase I were added to 50 μl of first strand reaction mixture in the order and mixed. After 2.5 hours of reaction at 16° C., it was cooled on ice.

(Blunting of cDNA Terminal)

Twenty-three μl of Blunting dNTP mixture solution and 2 μl of cloned Pfu DNA Polymerase were added to 200 μl of second strand buffer reaction mixture and the reaction was performed at 72° C. for 30 minutes. Two hundred μl of phenol/chloroform was added to it and stirred, then the aqueous layer was recovered by centrifugation. Two hundred μl of chloroform was added to it and stirred, then the aqueous layer was recovered by centrifugation. Twenty μl of 3M sodium acetate and 400 μl of 100% ethanol were added and it was left at −20° C. over night. The supernatant was removed by centrifugation and 400 μl of 70% ethanol was added to it. The supernatant was removed by centrifugation and it was dried in speed-back concentrator. The precipitate was dissolved in 9 μl of EcoRI adapter solution and 1 μl of the solution was preserved in −20° C. to confirm synthesis of the second Strand.

(Ligation of ECoRI Adapter)

One μl of 10× ligase buffer, 1 μl of 10 mM rATP and 1 μl of T4 DNA ligase are mixed to 8 μl of the reaction mixture remained in the above-mentioned operation and stirred. Then the mixture was treated at 8° C. for 2 days.

(Phosphorylation of EcoRI Terminal)

After incubating 11 μl of the resultant mixture described above at 70° C. for 30 minutes, it was left at room temperature for 5 minutes. One μl of 10× ligase buffer, 2 μl of 10 mM rATP, 6 μl of distilled water and 0.7 μl of T4 polynucleotide kinase were mixed and it was treated at 37° C. for 30 minutes. It was incubated at 70° C. for 30 minutes, then it was left at room temperature for 5 minutes.

(XhoI Cleavage)

Twenty-eight μl of XhoI buffer and 3 μl of XhoI were added to 20.7 μl of the resultant mixture and mixed, then it was reacted at 37° C. for 1.5 hours. After cooling at room temperature, 5 μl of 10×STE buffer (1M NaCl, 200 mM Tris-HCl pH 7.5, 100 mM EDTA) was added to it and mixed.

(Size Decomposition)

Size decomposition was performed according to the protocol of cDNA Spun Columns SizeSep 400 Spun Colums (Pharmacia). The column was re-suspended with 2 ml of STE buffer and it was allowed to elute. This operation was performed twice. A falcon tube was stood vertically and then it was centrifuged. A centrifugal tube, used for collection of the eluate, was set in the falcon tube and the cDNA sample was applied to the center of the column. Then 56.7 μl of cDNA fraction was recovered by centrifugation. Total volume of the fraction was adjusted to 200 μl with STE buffer. Two hundred μl of phenol/chloroform was added and stirred, then the aqueous layer was recovered in a new centrifugal tube by centrifugation. Two hundred μl of chloroform was added and stirred, then the aqueous layer was recovered in a new centrifugal tube by centrifugation. Four hundred μl of 100% ethanol was added to it and it was left at −20° C. over night. The supernatant was removed by centrifugation and the precipitate was dried in speed-back concentrator. It was dissolved in 5 μl of distilled water to obtain cDNA sample (10 ng/μl).

(Ligation of cDNA to Arm of Uni-ZAP XR Vector)

0.5 μl of 10× ligase buffer, 0.5 μl of 10 mM rATP, 1 μl of Uni-ZAP XR vector and 0.5 μl of T4 DNA ligase were added to 2.5 μl of the above-mentioned cDNA sample and mixed, then it was reacted at 4° C. for 2 days.

(Packaging)

Packaging was performed according to the protocol of MaxPlax Lambda Packaging Extract kit (EPICENTRE TECHNOLOGIES). After incubating 5 μl of the above-mentioned ligation sample at 65° C. for 15 minutes, it was left at room temperature for 5 minutes. The packaging extract was dissolved and 5 μl of the ligation sample was added to it and mixed, then it was incubated at 21.9° C. for 110 minutes. Five-hundred μl of SM buffer (5.8 g NaCl, 2.0 g magnesium sulfate heptahydrate, 50 ml Tris-HCl pH7.5, and 5 ml of 2% gelatin) and 25 μl of chloroform were gently mixed with it and centrifuged. Four hundred and fifty μl of the obtained supernatant was preserved at 4° C. as the packaging product.

(Screening of full-length C7 strand)

(Plating)

The host *Escherichia coli* XL1-Blue MRF, obtained by the stroke culture on LB-Tet (12.5 μg/ml), was cultured at 37° C. with shaking on 3 ml of LB plate, to reach OD600 value of 0.5. A hundred μl of the packaging product and 100 μl of the host bacteria were mixed, then incubated at 37° C. for 15 minutes. The mixed-culture liquid was mixed with 3 ml of LB top agar (liquor LB medium plus 0.7% agarose), which have been kept at 48° C., and plated on LB plate immediately. It was incubated at 37° C. over night.

(First Screening)

The above-mentioned plate was dried with air for 30 minutes. While cooling the plate on ice, nylon membrane (Hybond-N+, Amersham) was attached to the plate, then it was left for 2 minutes. The membrane was detached and it was immersed into denaturing buffer (0.5M sodium hydroxide, 1.5M sodium chloride) for 2 minutes. Moreover, it was immersed into neutralizing buffer (0.5M Tris-HCl pH 7.5, 1.5M NaCl) for 5 minutes. It was immersed into 20×SSC buffer (sodium chloride 175.3 g, sodium citrates 88.2 g) for 30 seconds, then it was dried on Kim towel. The DNA was crosslinked on the membrane by UV cross-linker at 70,000 μJ/cm². Pre-hybridization, hybridization using the gene fragment of C7-1 clone as a probe, washing, and detection of the signal were performed as described above in Northern hybridization.

(Second Screening)

Positive plaques obtained by the first screening were punched out by a pipette provided with a tip and suspended in 500 μl of SM buffer. Then 25 μl of chloroform was added to it and stirred. Plating, crosslinking to the membrane, pre-hybridization, hybridization, washing and detection of the signal were performed as described above.

(In Vivo Excision)

*Escherichia coli* XL1-BlueMRF described above and *Escherichia coli* SOLR obtained from the stroke culture on a LB-km (50 ng/ml) plate were cultured with shaking in 3 ml of LB medium at 37° C. over night. The plaque of the purpose obtained in the second screening was punched out as described above and it was suspended in SM buffer. Twenty μl of chloroform was added to it and then stirred. Subsequently, it was left at room temperature for 1 to 2 hours, with occasional stirring, to obtain phage stock 1. A hundred μl of *Escherichia coli* XL1-BlueMRF strain, 150 μl of the phage stock and 1 μl of ExAssist helper phage were mixed in a test tube and it was left at 37° C. for 15 minutes. After addition of 1 ml of LB medium, it was cultured with shaking at 37° C. for 2 to 3 hours. The culture mixture was poured into 1.5 ml centrifugal tube, it was incubated at 70° C. for 20 minutes, then it was cooled to room temperature. The supernatant was harvested by the centrifugation to obtain phage stock 2. Two-hundred μl of *Escherichia coli* SOLR strain and 50 μl of the phage stock 2 were mixed in 1.5 ml centrifugal tube and the mixture was left for 15 minutes. Fifty μl of the solution was plated on LB-Amp (50 μl/ml) plate and the plate was cultured at 37° C. over night.

(Confirmation of the Plasmid)

The plasmid of the colony was confirmed using colony PCR method. T3 primer (20mer, 5'-AATTAACCCTCACTAAAGGG-3', 3.2 μM, 1.5 μl), T7 primer (22mer, 5'-GTAATACGACTCACTATAGGGC-3', 3.2 μM, 1.5 μl), dNTPs (2.5 mM, 1.6 μl), 10×PCR buffer 2 μl, DNA polymerase (TAKARA Taq, 5 U/μl, 0.1 μl), 13.3 μl of distilled water and the colony picked up with a toothpick were put into 0.2 ml PCR tube and mixed well by tapping. Amplification was performed by PCR apparatus. After the reaction, electrophoresis was performed using 1% agarose/0.5×TBE gel. It was stained with ethidium bromide solution and the reaction product was confirmed on trans-illuminator. In the following, the colony PCR was performed with modification of conditions, such as primer and time of extension reaction, according to the occasions.

The conditions of the colony PCR

95° C. 1 minute

94° C. 30 seconds, 55° C. 30 seconds and 72° C. 2 minutes: 25 cycles

72° C. 7 minutes, 4° C. Infinity time (Preparation of Plasmid by Alkali Miniprep Method)

The single colony was inoculated in 3 ml of LB-Amp and it was incubated at 37° C. over night. The cultured medium was put into 1.5 ml tube and bacterial cells were harvested by centrifugation. The supernatant was removed and the *E. coli.* cells were suspended in 100 μl of solution I (50 mM glucose, 20 mM Tris-HCl pH 8.0, 10 mM EDTA pH 8.0). After addition of 200 μl of solution II (0.2 N NaOH, 1% SDS), the solution was mixed gently and settled on ice for 5 minutes. After addition of 150 μl of solution III (3 M potassium acetate, pH 4.8), the solution was mixed gently and settled on ice for 5 minutes. After centrifugation, the supernatant was harvested in a fresh 1.5 ml tube. Five hundred and fifty μl of phenol/chloroform was added to it and the solution was shaken for 5 minutes. It was centrifuged and the aqueous layer was harvested in a fresh 1.5 ml centrifugal tube. Nine hundred μl of 100% ethanol was added and it was left at room temperature for 3 minutes. After centrifugation, the supernatant was removed. Nine hundred μl of 70% ethanol was added, the supernatant was removed, and the precipitate was dried in speed-back concentrator. It was dissolved in 50 μl of TE, 1 μl of RNase (1 mg/ml) was added to it and the solution was left for 30 minutes. In the following, preparation of the plasmid by alkali miniprep method was performed by the procedure described above.

(Confirmation of Insertion by Restriction Enzyme Treatment)

Two μl of prepared plasmid solution, universal buffer H (TAKARA, 2 μl), EcoRI (TAKARA, 0.1 μl) and XhoI (TAKARA, 0.1 μl), and 15.8 μl of distilled water were put into a centrifugal tube and reaction was performed at 37° C. for 1 hour. After the reaction, gel electrophoresis was performed using 1% agarose/0.5×TBE. It was stained with ethidium bromide solution and the reaction product was confirmed on trance-illuminator. In the following, confirmation of the insertion, by restriction enzyme treatment, was performed using the procedure described above, with alteration of restriction enzymes according to the occasions.

(Preparation of the Plasmid by PEG Precipitation)

PEG/NaCl [1.6M/13% (w/v)] was added to 50 μl of plasmid solution prepared by alkali miniprep method and it was left at 4° C. over night. The supernatant was removed by centrifugation (15,000 rpm, 20 minutes, 4° C.), 250 μl of 70% ethanol was added to the precipitate and centrifugation was performed again. The supernatant was removed, the precipitate was dried in speed-back concentrator and dissolved in 40 μl of TE. Hereafter, preparation of the plasmid using PEG was performed by the method described above.

(Determination of DNA Sequence of C7 Full-Length cDNA Strand)

BigDye Terminator Ready Reaction Mixture (PE applied system, 8 μl), T7 or T3 primer (3.2 μM, 1 μl) and the plasmid (corresponding to approximately 500 ng) prepared using PEG were put into 0.2 ml PCR tube, then distilled water was added to it, resulting to total volume of 20 μl. After the reaction by PCR apparatus, the total solution was transferred to 1.5 ml tube for centrifugation. Two μl of 3M NaOAc (pH 5.2) and 50 μl of ice-cold 100% ethanol were added to it, then it was left at −80° C. for more than 20 minutes. The supernatant was removed by centrifugation, 250 μl of 70% ethanol was added to the precipitate, then centrifugation was performed again. After drying the precipitate in speed-back concentrator, it was dissolved in 12 μl of Templete Suppression Reagent (TSR, PE applied system). After heat denaturation at 95° C. for 3 minutes, it was immediately cooled on ice.

The conditions of PCR

96° C. 10 seconds, 50° C. 5 seconds, and 60° C. 4 minutes: 25 cycles

4° C., Infinity time

Furthermore, the base sequence was determined by fluorescence capillary sequencer (ABI PRISM 310 Genetic-Analyzer PE applied system). The primers used for the sequence determination are as follows.

C7F1: (29mer, 5'-GCTCCTATCAATTCGTCACAGTATATTCC-3', 3.2 μM, 1 μl)

C7F2: (25mer, 5'-CCAGGCATTTCATCAAACAAGTTCG-3', 3.2 μM, 1 μl)

C7R1: (22mer, 5'-CTCCACCTATTCCTATACCGCC-3', 3.2 μM, 1 μl)

C7R2: (26mer, 5'-GCACTCACCCCCACGACTCCGGTCGC-3', 3.2 μM, 1 μl)

(Functional Analysis of C7 Gene Product)

Figure 1:
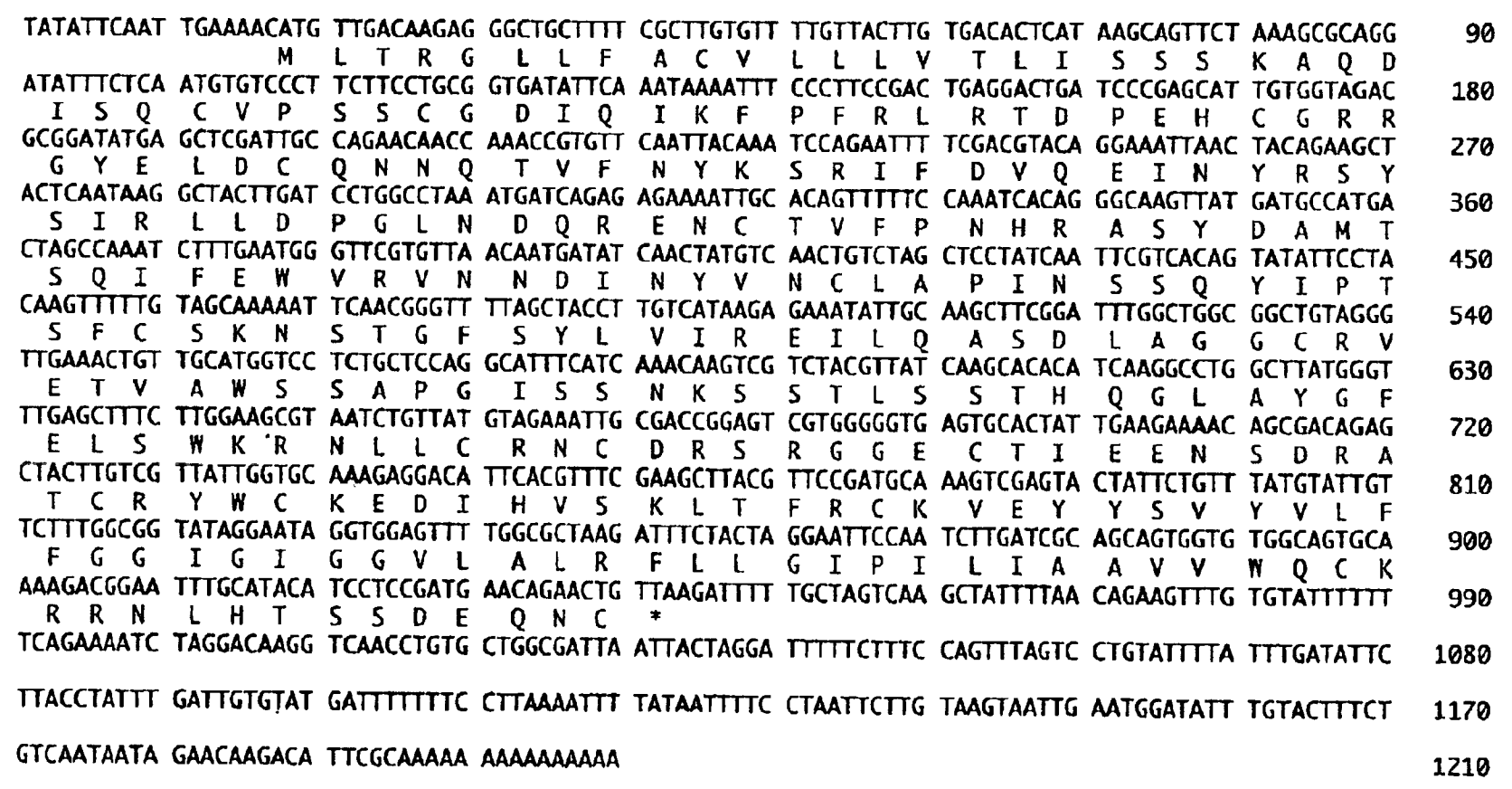

As the result of sequence determination of full length C7 gene, it was found that the full length comprising 1210 bp, which encodes 308 amino acids (FIG. 1). According to the result of homology search by BLAST, it was shown that the amino acid sequence of C7 exhibited significant homology to receptor-like proteins. Moreover, the localization of C7 protein in the cell was estimated by PSORT. As the result, it contained hydrophobic signal which cleaves at the 24th amino acid, single transmembrane domain having helix structure and hydrophilic cytoplasmic region. The predicted functional region of C7 gene product and its hydrophobic profile are shown in FIG. 2.

(Homology of C7 Protein and Receptor-Like Kinases)

As described above, from the result of homology search and predicted structure, it was suggested that protein encoded by the C7 gene was a transmembrane protein. Furthermore, it was suggested that C7 protein exhibited significant homology to receptor-like kinases (RLK) from database search. The amino acid alignment of the region exhibiting homology to LRK10, which is product of wheat Lr10 disease resistance-gene locus, is shown in FIG. 3. In FIG. 3, the regions surrounded by squares indicate amino acids having identity among the three proteins and the dotted regions indicate those having high homology among the three proteins.

(Localization in a Plant Cell)

Localization of C7 protein in a plant cell was examined using C7-GFP (Green Fluorescent Protein) fusion protein. C7/GFP fusion plasmid was coated to aurum particles and they were incorporated into plant tissue (onion) by particle gun method. After incubation for overnight, observation using fluorescence microscope revealed that the C7-GFP fusion protein localized on plasma membrane (FIG. 4). FIG. 4 shows GFP (left) temporarily expressed on onion epidermal cell and fluorescence signal of the C7-GFP fusion protein (right).

From features of C7 protein described above, it was suggested that C7 protein would be type I transmembrane protein. In spite of having homology with receptor-like kinases, a cytoplasmic region having kinase sequence was not found in C7 protein. The stress sensor proteins are known to form dimers and interact with other proteins to transduce signals to the downstream of transduction pathway in a cell. Therefore, it is assumed that C7 protein may be an osmotic-pressure sensor which forms a dimer. Moreover, it is possible that C7 protein may transduce signals by interaction with certain target protein in a cell, which result in expression control of downstream genes responsible for other stress response.

(Characterization of C7 expression on stress response)

Figure 5:
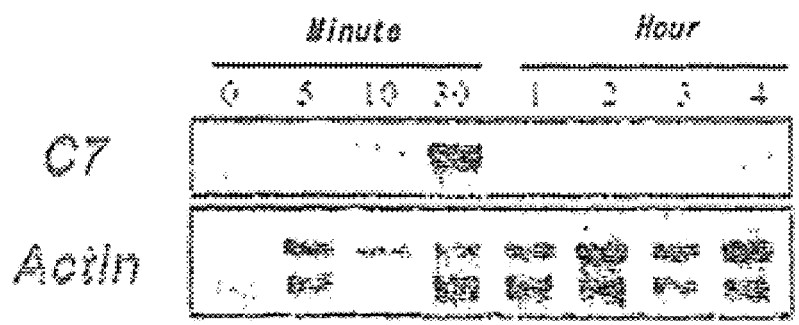
FIG. 5 is a figure showing time course of mRNA level of C7 gene after exposure to injury stress, detected by Northern blotting analysis.

The characterization of expression of C7 gene on stress response was examined by Northern hybridization. That is, time course of C7 gene expression was investigated on a leaf exposed to injury stress. C7 gene exhibited transient expression, that is, expression of C7 gene initiated approximately at 10 minutes, reached to maximum at 30 minutes and disappeared at 4 hours (FIG. 5). The lower data in FIG. 5 shows the result of actin expression, the control gene exhibiting constitutive expression. Thus, C7 gene is expressed transiently at early stage of injury stress response, indicating importance of this gene for a plant.

Figure 6:
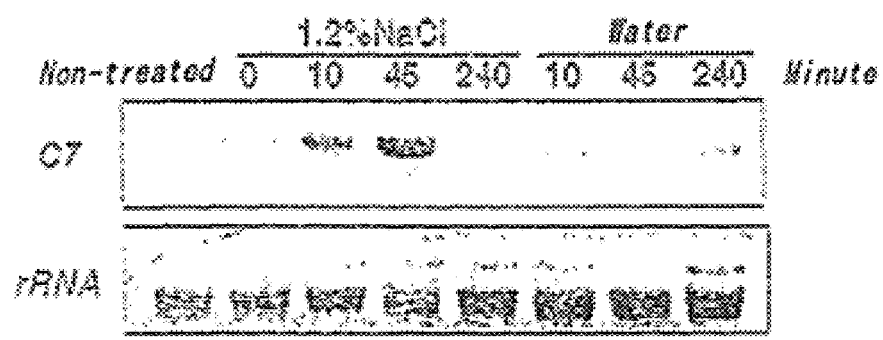
FIG. 6 is a figure showing time course of mRNA level of C7 gene after exposure to salt stress, detected by Northern blotting analysis.
Figure 7:
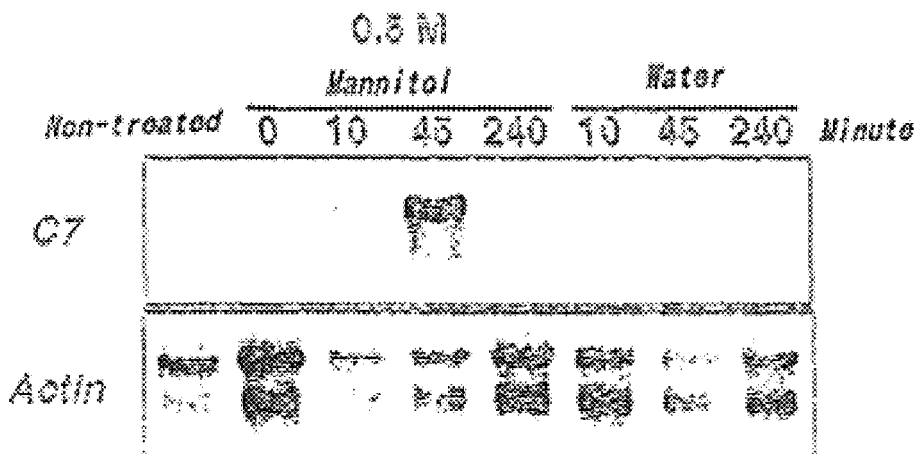
FIG. 7 is a figure showing time course of mRNA level of C7 gene after exposure to osmotic pressure stress, detected by Northern blotting analysis.

The influence of aqueous environment of a cell, on the expression of C7 gene, was examined. That is, influence of salt stress was examined with 1.2% NaCl and that of osmotic-pressure stress was examined with 500 mM mannitol. An intact leaf was cut off from a plant and immersed in water for 4 hours to avoid influence of mechanical injury stress on C7 gene expression, then it was re-immersed in each solution for stress treatment. Consequently, transient expression, caused by each of salt stress and osmotic-pressure stress, was found 45 minutes after stress treatment. Alteration of mRNA level, caused by salt stress of 1.2% NaCl treatment which was detected by Northern hybridization, was shown in FIG. 6. Alteration of mRNA level, caused by osmotic-pressure stress of 500 mM mannitol treatment, was also shown in FIG. 7. The results of detection of rRNA and actin, the control gene exhibiting constitutive expression, were shown in the lower columns of FIGS. 6 and 7, respectively. That is, it was shown that the expression of C7 gene increased in response to aqueous environmental stress. Furthermore, the response of C7 gene to dehydration stress and low temperature stress was also examined. As same in the case of salt stress and osmotic-pressure stress, an intact whole leaf was cut off from a plant, it was immersed in water for 4 hours, and then exposed to low-temperature stress under 4° C. As the result, although the expression of C7 gene was induced by low-temperature stress, C7 gene was not induced by hydration stress.

According to this invention, C7 gene, a novel gene encoding a receptor-like protein which is induced in response to injury stress, osmotic pressure stress, salt stress or low-temperature stress, is provided. Moreover, a polypeptide encoded by said gene is provided.

What is claimed is:

1. An isolated DNA molecule comprising the nucleotide sequence of SEQ ID NO:2.

2. An isolated DNA molecule consisting of nucleotides 1 to 1210 of SEQ ID NO:3.

* * * * *

SEQUENCE LISTING

```
<160> NUMBER OF SEQ ID NOS: 3

<210> SEQ ID NO 1
<211> LENGTH: 308
<212> TYPE: PRT
<213> ORGANISM: Nicotiana tabacum
<220> FEATURE:
<221> NAME/KEY: PEPTIDE
<222> LOCATION: (277)
<223> OTHER INFORMATION: Amino acid 277 is "Xaa" wherein "Xaa" = any
      amino acid.

<400> SEQUENCE: 1

Met Leu Thr Arg Gly Leu Leu Phe Ala Cys Val Leu Leu Leu Val Thr
1               5                   10                  15
```

```
Leu Ile Ser Ser Ser Lys Ala Gln Asp Ile Ser Gln Cys Val Pro Ser
                 20                  25                  30
Ser Cys Gly Asp Ile Gln Ile Lys Phe Pro Phe Arg Leu Arg Thr Asp
             35                  40                  45
Pro Glu His Cys Gly Arg Gly Tyr Glu Leu Asp Cys Gln Asn Asn
         50                  55                  60
Gln Thr Val Phe Asn Tyr Lys Ser Arg Ile Phe Asp Val Gln Glu Ile
65                   70                  75                  80
Asn Tyr Arg Ser Tyr Ser Ile Arg Leu Leu Asp Pro Gly Leu Asn Asp
                 85                  90                  95
Gln Arg Glu Asn Cys Thr Val Phe Pro Asn His Arg Ala Ser Tyr Asp
                100                 105                 110
Ala Met Thr Ser Gln Ile Phe Glu Trp Val Arg Val Asn Asn Asp Ile
            115                 120                 125
Asn Tyr Val Asn Cys Leu Ala Pro Ile Asn Ser Ser Gln Tyr Ile Pro
130                 135                 140
Thr Ser Phe Cys Ser Lys Asn Ser Thr Gly Phe Ser Tyr Leu Val Ile
145                 150                 155                 160
Arg Glu Ile Leu Gln Ala Ser Asp Leu Ala Gly Gly Cys Arg Val Glu
                165                 170                 175
Thr Val Ala Trp Ser Ser Ala Pro Gly Ile Ser Ser Asn Lys Ser Ser
            180                 185                 190
Thr Leu Ser Ser Thr His Gln Gly Leu Ala Tyr Gly Phe Glu Leu Ser
            195                 200                 205
Trp Lys Arg Asn Leu Leu Cys Arg Asn Cys Asp Arg Ser Arg Gly Gly
    210                 215                 220
Glu Cys Thr Ile Glu Glu Asn Ser Asp Arg Ala Thr Cys Arg Tyr Trp
225                 230                 235                 240
Cys Lys Glu Asp Ile His Val Ser Lys Leu Thr Phe Arg Cys Lys Val
                245                 250                 255
Glu Tyr Tyr Ser Val Tyr Val Leu Phe Phe Gly Gly Ile Gly Ile Gly
            260                 265                 270
Gly Val Leu Ala Xaa Arg Phe Leu Leu Gly Ile Pro Ile Leu Ile Ala
            275                 280                 285
Ala Val Val Trp Gln Cys Lys Arg Arg Asn Leu His Thr Ser Ser Asp
290                 295                 300
Glu Gln Asn Cys
305

<210> SEQ ID NO 2
<211> LENGTH: 927
<212> TYPE: DNA
<213> ORGANISM: Nicotiana tabacum

<400> SEQUENCE: 2
atgttgacaa gagggctgct tttcgcttgt gttttgttac ttgtgacact cataagcagt    60
tctaaagcgc aggatatttc tcaatgtgtc ccttcttcct gcggtgatat tcaaataaaa   120
tttcccttcc gactgaggac tgatcccgag cattgtggta gacgcggata tgagctcgat   180
tgccagaaca accaaaccgt gttcaattac aaatccagaa ttttcgacgt acaggaaatt   240
aactacagaa gctactcaat aaggctactt gatcctggcc taaatgatca gagagaaaat   300
tgcacagttt ttccaaatca cagggcaagt tatgatgcca tgactagcca aatctttgaa   360
tgggttcgtg ttaacaatga tatcaactat gtcaactgtc tagctcctat caattcgtca   420
```

-continued

```
cagtatattc ctacaagttt ttgtagcaaa aattcaacgg gttttagcta ccttgtcata    480
agagaaatat tgcaagcttc ggatttggct ggcggctgta gggttgaaac tgttgcatgg    540
tcctctgctc caggcatttc atcaaacaag tcgtctacgt tatcaagcac acatcaaggc    600
ctggcttatg ggtttgagct ttcttggaag cgtaatctgt tatgtagaaa ttgcgaccgg    660
agtcgtgggg gtgagtgcac tattgaagaa aacagcgaca gagctacttg tcgttattgg    720
tgcaaagagg acattcacgt ttcgaagctt acgttccgat gcaaagtcga gtactattct    780
gtttatgtat tgttctttgg cggtatagga ataggtggag ttttggcgct aagatttcta    840
ctaggaattc caatcttgat cgcagcagtg gtgtggcagt gcaaaagacg gaatttgcat    900
acatcctccg atgaacagaa ctgttaa                                       927
```

<210> SEQ ID NO 3
<211> LENGTH: 1210
<212> TYPE: DNA
<213> ORGANISM: Nicotiana tabacum

<400> SEQUENCE: 3

```
tatattcaat tgaaaacatg ttgacaagag ggctgctttt cgcttgtgtt ttgttacttg     60
tgacactcat aagcagttct aaagcgcagg atatttctca atgtgtccct tcttcctgcg    120
gtgatattca aataaaattt cccttccgac tgaggactga tcccgagcat tgtggtagac    180
gcggatatga gctcgattgc cagaacaacc aaaccgtgtt caattacaaa tccagaattt    240
tcgacgtaca ggaaattaac tacagaagct actcaataag gctacttgat cctggcctaa    300
atgatcagag agaaaattgc acagttttc caaatcacag ggcaagttat gatgccatga    360
ctagccaaat ctttgaatgg gttcgtgtta acaatgatat caactatgtc aactgtctag    420
ctcctatcaa ttcgtcacag tatattccta caagtttttg tagcaaaaat tcaacgggtt    480
ttagctacct tgtcataaga gaaatattgc aagcttcgga tttggctggc ggctgtaggg    540
ttgaaactgt tgcatggtcc tctgctccag gcatttcatc aaacaagtcg tctacgttat    600
caagcacaca tcaaggcctg gcttatgggt ttgagctttc ttggaagcgt aatctgttat    660
gtagaaattg cgaccggagt cgtggggtg agtgcactat tgaagaaaac agcgacagag    720
ctacttgtcg ttattggtgc aaagaggaca ttcacgtttc gaagcttacg ttccgatgca    780
aagtcgagta ctattctgtt tatgtattgt tctttggcgg tataggaata ggtggagttt    840
tggcgctaag atttctacta ggaattccaa tcttgatcgc agcagtggtg tggcagtgca    900
aaagacggaa tttgcataca tcctccgatg aacagaactg ttaagatttt tgctagtcaa    960
gctattttaa cagaagtttg tgtatttttt tcagaaaatc taggacaagg tcaacctgtg   1020
ctggcgatta attactagga ttttctttc cagtttagtc ctgtatttta tttgatattc   1080
ttacctattt gattgtgtat gatttttttc cttaaaattt tataattttc ctaattcttg   1140
taagtaattg aatggatatt tgtactttct gtcaataata gaacaagaca ttcgcaaaaa   1200
aaaaaaaaaa                                                         1210
```